US012775010B2

(12) United States Patent
Lee et al.

(10) Patent No.: US 12,775,010 B2
(45) Date of Patent: Oct. 27, 2026

(54) CARTRIDGE FOR SANDWICH ELISA PRE-LOADED WITH ANTIGEN CUSTOMIZED DETECTION REAGENT AND SANDWICH ELISA DEVICE USING THE CARTRIDGE

(71) Applicant: REVOSKETCH INC., Yuseong-gu (KR)

(72) Inventors: Sung Woon Lee, Yuseong-gu (KR); Tae Ho Yoon, Seo-gu (KR); Hyo Jun Kim, Sejong-si (KR)

(73) Assignee: REVOSKETCH INC., Daejeon (KR)

( * ) Notice: Subject to any disclaimer, the term of this patent is extended or adjusted under 35 U.S.C. 154(b) by 1063 days.

(21) Appl. No.: 17/916,330

(22) PCT Filed: Apr. 3, 2020

(86) PCT No.: PCT/KR2020/004538

§ 371 (c)(1),
(2) Date: Sep. 30, 2022

(87) PCT Pub. No.: WO2021/201324

PCT Pub. Date: Oct. 7, 2021

(65) Prior Publication Data

US 2023/0028665 A1 Jan. 26, 2023

(51) Int. Cl.

| | |
|---|---|
| ***G01N 33/543*** | (2006.01) |
| ***B01L 3/00*** | (2006.01) |
| ***B01L 3/02*** | (2006.01) |

(52) U.S. Cl.

CPC ...... *G01N 33/54366* (2013.01); *B01L 3/0244* (2013.01); *B01L 3/50853* (2013.01);

(Continued)

(58) Field of Classification Search

CPC ................................................ G01N 33/54366

See application file for complete search history.

(56) References Cited

U.S. PATENT DOCUMENTS

| | | | | |
|---|---|---|---|---|
| 2003/0203491 | A1 * | 10/2003 | Andrevski | G01N 35/0098 436/175 |
| 2012/0149035 | A1 | 6/2012 | Burd et al. | |

(Continued)

FOREIGN PATENT DOCUMENTS

| | | | | |
|---|---|---|---|---|
| KR | 101579327 B1 | 12/2015 | | |
| WO | WO-2006005483 A1 * | 1/2006 | | G01N 27/3272 |
| WO | 2014198836 A1 | 12/2014 | | |

OTHER PUBLICATIONS

International Search Report in International Patent Application No. PCT/KR2020/004538 mailed Dec. 28, 2020 (5 pp.).

(Continued)

*Primary Examiner* — Charles Capozzi
*Assistant Examiner* — Velvet Elizabeth Heron
(74) *Attorney, Agent, or Firm* — Nixon Peabody LLP

(57) ABSTRACT

The present invention relates to a cartridge for sandwich ELISA pre-loaded with antigen customized detection reagent to more efficiently perform the sandwich ELISA and a sandwich ELISA device using the cartridge. A cartridge for sandwich ELISA according to the present invention is arranged in rows and columns, and includes a body in which wells accommodating reagents are formed, a pin-assy including pins that have a capture antibody coated on one ends thereof, and a provider that moves the pin-assy to provide the well with the pin to allow the reagents and the capture antibody to be into contact and react with each other.

8 Claims, 5 Drawing Sheets

(52) U.S. Cl.
CPC ..... *B01L 3/50857* (2013.01); *B01L 2300/044* (2013.01); *B01L 2300/0672* (2013.01); *G01N 2470/04* (2021.08)

(56) References Cited

U.S. PATENT DOCUMENTS

2017/0328901 A1 11/2017 Castrop
2018/0015437 A1 1/2018 Lammertyn et al.
2019/0369134 A1 12/2019 Wu et al.
2019/0391142 A1 12/2019 Jeon et al.

OTHER PUBLICATIONS

Written Opinion in International Patent Application No. PCT/KR2020/004538 mailed Dec. 28, 2020 (5 pp.).
European search report for Application No. 20929166.5, mailed Nov. 10, 2023.

* cited by examiner

CARTRIDGE FOR SANDWICH ELISA PRE-LOADED WITH ANTIGEN CUSTOMIZED DETECTION REAGENT AND SANDWICH ELISA DEVICE USING THE CARTRIDGE

CROSS-REFERENCE TO RELATED APPLICATIONS

This application is the United States National Phase of International Application No.: PCT/KR2020/004538, filed Apr. 3, 2020, the entire contents of which are herein incorporated by reference in its entirety.

TECHNICAL FIELD

The present invention relates to a cartridge for sandwich ELISA most commonly used among enzyme linked immunosorbent assays (ELISA) and a sandwich ELISA device using the cartridge.

BACKGROUND ART

Enzyme linked immunosorbent assay (ELISA), which is a method of confirming an antigen-antibody reaction by conjugating an enzyme to an antibody, is an immunoassay that shows high detection ability for a specific antibody or antigen. The ELISA is the most widely used antigen-antibody assay method because the ELISA has high detection ability, is simple and inexpensive, and can perform mass analysis.

Many modifications of the ELISA have been developed and used in different situations, but have the same four basic elements: A difference between these modifications comes from the difference between these basic elements.

① Coating/Capture: direct or indirect immobilization of antigens to the surface of polystyrene microplate wells.

② Plate Blocking: addition of irrelevant protein or other molecule to cover all unsaturated surface-binding sites of the microplate wells.

③ Probing/Detection: incubation with antigen-specific antibodies that affinity-bind to the antigens.

④ Signal Measurement: detection of the signal generated via the direct or secondary tag on the specific antibody.

More specifically, there are several types of ELISA as follows.

1) Direct ELISA

Direct ELISA is a method of directly conjugating an enzyme to an antibody that reacts with an antigen. In order to perform the direct ELISA, a method of demanding a labeled antibody for an antibody, immobilizing an antigen on a plate, and injecting a labeled antibody is used.

2) Indirect ELISA

Indirect ELISA is a method of using an enzyme that is not conjugated to an antibody (primary antibody) bound to an antigen, but is conjugated to an antibody (secondary antibody) bound to the primary antibody. In general, the indirect ELISA is commercialized and sold as an enzyme conjugated anti-isotype antibody type, and an experimenter purchases and uses an enzyme conjugated antibody that meets the isotype of the primary antibody that he/she uses.

3) Sandwich ELISA

The sandwich ELISA is a method in which an antibody against an antigen is first bound to a plate, and the antigen is bound to the antibody and then tested in a direct or indirect method in order to better immobilize the antigen on the plate. The sandwich ELISA is used when the amount of antigen is small or when the antigen contained in an unknown sample is tested, and requires two antigen-specific antibodies.

4) Competitive ELISA

The competitive ELISA is achieved by competition between two antigens for one identical binding site of an antibody. One of the two antigens is an antigen labeled by an isotope or an enzyme, and the other is unlabeled. The competitive ELISA requires a sample that contains a labeled antigen, a non-labeled antigen (that is, antigen to be quantified) to make a standard curve, a monoclonal antibody (or antiserum) specifically bound to the antigen, and an antigen. The antigen contained in the unknown sample is quantified by the standard curve using a weak label signal detected in a reaction binding substance by the reaction of the antibody with the unlabeled antigen contained in the sample. According to the competition principle, the free binding site of the antibody becomes a limit factor in the reaction solution.

Among them, the sandwich ELISA has high sensitivity, and therefore is considerably widely used. The sandwich ELISA process will be described in detail as follows.

① Coating: Coat a capture antibody on a plate. In general, in the case of an experimental kit, the capture antibody is provided in a state already coated on the plate.

② Plate Blocking: Block other surfaces for specific binding to a sample antigen. In general, in the case of the experimental kit, the capture antibody is coated on the plate and then provided in the blocked state.

③ Detection: In the case of the direct method, enzymes are conjugated to the detection antibody, and therefore it is possible to immediately perform the detection by adding only a substrate. In the case of the indirect method, it is possible to perform detection by adding the substrate after a process of binding an enzyme conjugated secondary antibody to the detection antibody is subjected.

④ Signal Measurement: Measure an optical density value using an ELISA reader.

The inference can be made from the above processes. In addition, as is well known from the actual process of the ELISA, in the ELISA, the processes of filling, emptying, and washing a variety of experimental reagents (detect antibody, washing buffer, HRP, TMB, and the like) are repeated on the plate coated with the capture antibody several times. It is necessary to repeatedly perform such a complicated process, and as a result, it is true that ELISA has a very high risk of human error.

To reduce this risk, attempts have been made to automate the ELISA process. However, since the conventional ELISA automation devices include a method of injecting necessary reagents step by step, there is a problem in that the device becomes large and expensive because it requires precise positioning and injection amount control.

DISCLOSURE

Technical Problem

The present invention has been devised to solve the problems of the related art as described above, and an object of the present invention is to provide a cartridge for sandwich ELISA pre-loaded with antigen customized detection reagent to more efficiently perform the sandwich ELISA and a sandwich ELISA device using the cartridge.

Technical Solution

In one general aspect, a cartridge 100 for sandwich ELISA may include: a body 110 that has a plurality of wells 111 arranged in rows and columns in a width direction and a length direction, having reagents accommodated therein, and formed on a top surface thereof; a pin-assy 120 that includes a plurality of pins 121 extending in one direction and having a capture antibody coated on some areas of one end thereof and a single bar 122 extending in the width direction and coupled to the other end of the pins 121 so that the pins 121 are arranged to correspond to positions of the wells 111 included in the row; and a provider 130 that extends in the width direction to support the pin-assy 120 and is movably formed in the length direction from the top surface of the body 110 to provide the row composed of the pins 121 with the row composed of the wells 111.

In addition, according to the cartridge 100 for sandwich ELISA, the bar 122 may be rotatably coupled to the provider 130, and the one end of the pin 121 may be immersed in or taken out from the well 111 by the rotation of the bar 122.

In addition, according to the cartridge 100 for sandwich ELISA, the bar 122 may be rotated by the movement of the provider 130 in the length direction, the pins 121 may protrude in an opposite direction to a traveling direction of the provider 130 to be supported on the top surface of the body 110, when the provider 130 is arranged at a position where the wells 111 do not exist on the top surface of the body 110, and the one end of the pins 121 may be immersed in the wells 111 by the rotation of the bar 122, when the provider 130 is arranged at a position where the wells 111 exist on the top surface of the body 110.

In this case, according to the cartridge 100 for sandwich ELISA, the top surface of the membrane 112 may be covered with a membrane 112 to prevent the reagents accommodated in the wells 111 from being separated, and the one end of the pins 121 may be immersed in the wells 111 while crushing the membrane 112, when the bar 122 is rotated by the movement of the provider 130 in the length direction.

In addition, the pin 121 may include a tearer 123 whose one end surface is inclined so that a tip thereof is sharply formed.

In addition, the pin 121 may include sample-stations 124 recessed in a dish form that are formed in some areas on which the capture antibody is coated.

In this case, the sample-station 124 may be formed on an opposite side where the tearer 123 is formed.

In addition, the provider 130 may be provided with a pair of holes 131 that is formed on both ends of thereof in the width direction and grooves 132 that communicate with the pair of holes 131 and extend in the width direction so that the bar 122 may be accommodated in the groove 132 and both ends of the bar 122 may be fitted into the pair of holes 131 to replaceably couple the pin-assy 120 to the provider 130.

In addition, the provider 130 may be provided with a pair of guides 133 that is formed on a surface of an opposite direction to the traveling direction of the both ends of thereof in the width direction, the pair of guides 133 regulating the rotation of the pins 121, and a width between the pair of guides 133 may be formed to be the same as that of a row of any one of the wells 111 so that the guide 133 may prevent the pins 121 from being deviated from a fixed position corresponding to the positions of the wells 111 in the width direction.

In addition, according to the cartridge 100 for sandwich ELISA, a pair of rails 113 extending in the length direction may be formed at the both ends of the body 110 in the width direction and sliders 134 may be formed at lower ends of the both ends of the provider 130 in the width direction to engage with the rails 113 so that the rails 113 and the sliders 134 engage with each other to slidably move the provider 130 in the length direction on the body 110.

In another general aspect, a sandwich ELISA device according to the present invention may include the cartridge 100 for sandwich ELISA as described above.

Advantageous Effects

According to the present invention, the pins coated with the capture antibody are stepwise inserted into the wells pre-loaded with the reagents required for the sandwich ELISA. Accordingly, according to the present invention, it is possible to very easily simplify and automate the processes of adding, reacting, emptying, and washing the reagents, and adding other reagents again as in the related art. In particular, in the related art, the capture antibody was coated on the plate, and as a result, there is a high risk of human error in the process of sequentially adding several reagents to the plate and washing the reagents, but according to the present invention, required reagents are stepwise pre-loaded into the wells in accordance with the pre-designed experimental stage, and as a result, the risk of human error is basically eliminated by pre-loading the reagents. That is, according to the present invention, there is an effect of maximizing the accuracy, promptness, and efficiency of the sandwich ELISA.

In addition, according to the present invention, appropriate reagents can be pre-loaded according to the antigen to be detected. Accordingly, the customized cartridge for the detection antigen can be easily manufactured. In addition, the cartridge according to the present invention has a simple configuration and is easy to manufacture. As such, as the cartridge in which the required reagent is pre-loaded, the analytical device can also be configured simply and compactly to have only basic functions, such that the sandwich ELISA device itself can be reduced in size and cost.

BEST MODE

Hereinafter, a cartridge for a sandwich ELISA pre-loaded with an antigen customized detection reagent according to the present invention having the above-described configuration and a sandwich ELISA device using the cartridge will be described in detail with reference to the accompanying drawings.

Figure 1:
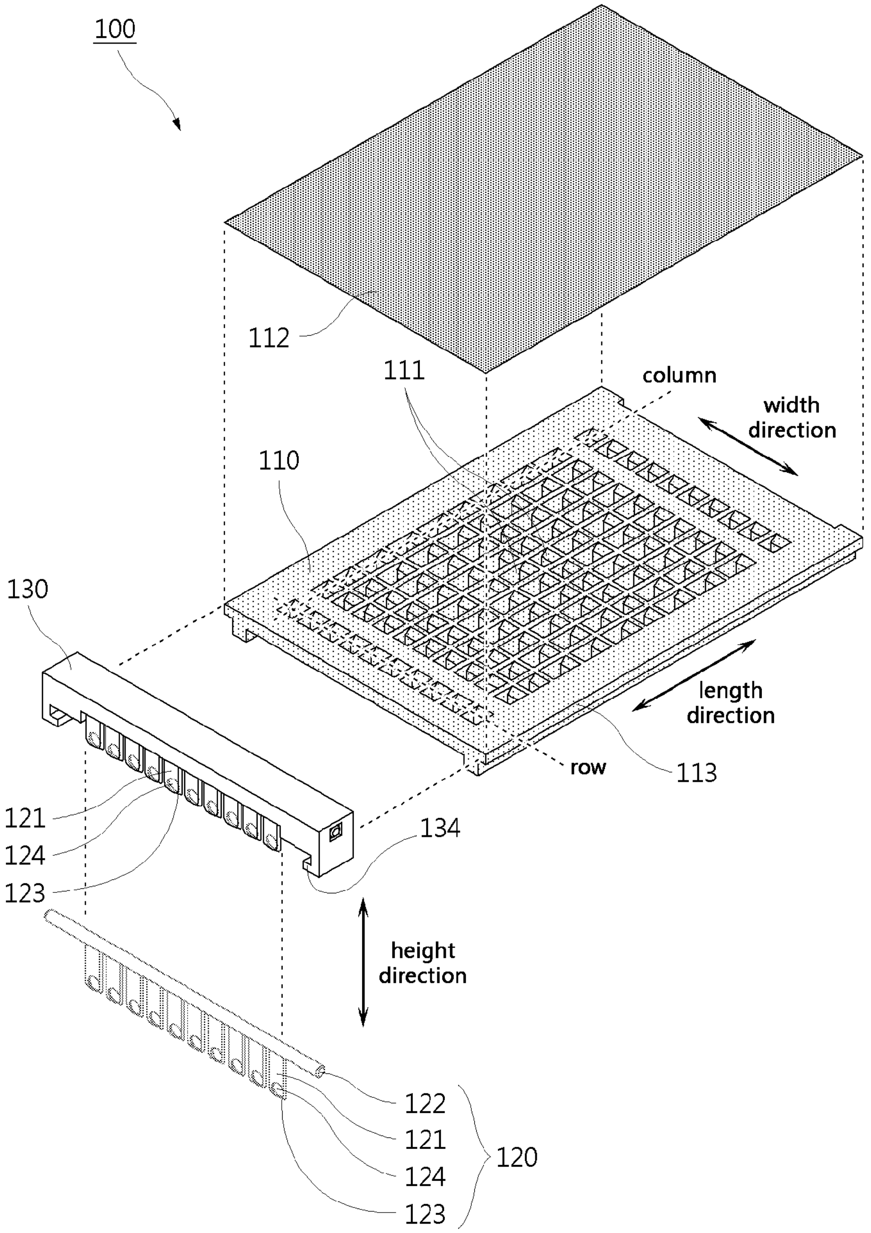
FIG. 1 is an exploded perspective view of a cartridge for sandwich ELISA according to the present invention.

FIG. 1 is an exploded perspective view of the cartridge for sandwich ELISA according to the present invention. As shown in FIG. 1, the cartridge 100 for sandwich ELISA according to the present invention may include a body 110, a pin-assy 120, and a provider 130.

The body 110 has a plurality of wells 111 that are arranged in rows and columns in a width direction and a length direction, and formed on a top surface thereof. Reagents are accommodated in the wells 111, in which the reagents accommodated in the wells 111 can be any reagents except for a sample to be tested among various reagents required for a sandwich ELISA process. In addition, as shown in FIG. 1, the plurality of wells 111 may be the same or different in size from each other, which may be determined according to the amount of reagent required in the ELISA process. In addition, it is preferable that a membrane 112 is covered on the top surface of the body 110 to prevent the reagents accommodated in the wells 111 from being separated.

As shown, the pin-assy 120 includes a plurality of pins 121 and a bar 122 that is coupled to the pins 121 to fixedly support the pins 121. The pins 121 are formed to extend in one direction, and some areas of one ends thereof are coated with a capture antibody. In this case, as shown in FIG. 1, sample-stations 124 recessed in a dish form may be formed in some areas on which the capture antibody is coated. The pin 121 is provided with the sample-station 124, and as a result, the capture antibody can be more stably immobilized on the pin 121. On the other hand, the other end of the pins 121 is coupled to a single bar 122, in which the bar 122 serves to allow the pins 121 to be arranged to correspond to positions of the wells 111 included in any one of rows of the pins 121.

The provider 130 extends in the width direction to support the pin-assy 120 and is movably formed in the length direction from the top surface of the body 110. As described above, since the plurality of pins 121 included in the pin-assy 120 are arranged to correspond to the positions of the wells 111 included in any one row, when the positions of the pins 121 overlap the positions of the wells 111 forming any one row while the provider 130 moves the pin-assy 120, the pins 121 may be immersed in the wells 111. That is, the provider 130 serves to provide a column composed of the wells 111 with a column composed of the pins 121.

In summary, the cartridge 100 for sandwich ELISA according to the present invention is arranged in rows and columns, and includes the body 110 in which the wells 111 accommodating reagents are formed, the pin-assy 120 including the pins 121 that have the capture antibody coated on one ends thereof, and the provider 130 that moves the pin-assy 120 to provide the well 111 with the pin 121 to allow the reagents and the capture antibody to be into contact and react with each other. In the related art, the ELISA was progressed by repeatedly performing processes of immobilizing the capture antibody on the plate, performing the reaction with the reagent by filling the plate with the reagent, emptying the reagent after the reaction for the next step, and washing the plate. However, in the present invention, the reagent is pre-loaded into the wells 111 on the body 110, and the capture antibody is coated on the pin 121. In this state, when the provider 130 moves the pin-assy 120 in the length direction of the body 110, the rows composed of the pins 121 may be sequentially immersed in or taken out from the rows composed of the wells 111. In other words, in the conventional process, a complex process of filling and discarding several reagents in and from the plate on which the capture antibody is immobilized is replaced with a simple process of sequentially containing or taking out the pins 121 on which the capture antibody is immobilized in or from the wells 111 pre-loaded with several reagents. There is a problem in that in the conventional complex process, the risk of human error and the like is very high, and when the process is automated as it is, a motion of a person should be replaced with a machine, and as a result, the device is very complicated. However, the present invention fundamentally prevents these problems because the process itself is much simplified, and as a result, the accuracy, promptness, and efficiency of the ELISA are maximized. In addition, the sandwich ELISA device including the cartridge 100 for sandwich ELISA according to the present invention can be made in a much simpler configuration than the conventional automation device by simply configuring the analytical device in a very compact form so as to have only basic functions, such that the sandwich ELISA device itself can be compact and inexpensive.

Hereinafter, embodiments of the pin-assy 120 and the provider 130 will be described in more detail.

As described above, in the present invention, the rows (hereinafter referred to as "pin-row") composed of the pins 121 are provided to the row (hereinafter referred to as "well-row") composed of the wells 111, and are sequentially provided to the well 111-rows arranged in the length direction. Of course, even if the device is configured to move each pin 121 by a separate actuator, the above operation can be realized. In this case, however, the device may be unnecessarily excessively complicated. In realizing the above-described operation, it is preferable that the pins 121 forming one row are interlocked with each other to make the same movement. In the present invention, as the simplest structure for realizing such an operation, the same structure as the pin-assy 120 as shown in FIG. 1 and the like, that is, a structure in which the plurality of the pins 121 are coupled to and fixed to the single bar 122 while being arranged in one row is employed. According to this structure, by operating only the bar 122, the plurality of pins 121 can realize the same movement at a time.

Figure 2:
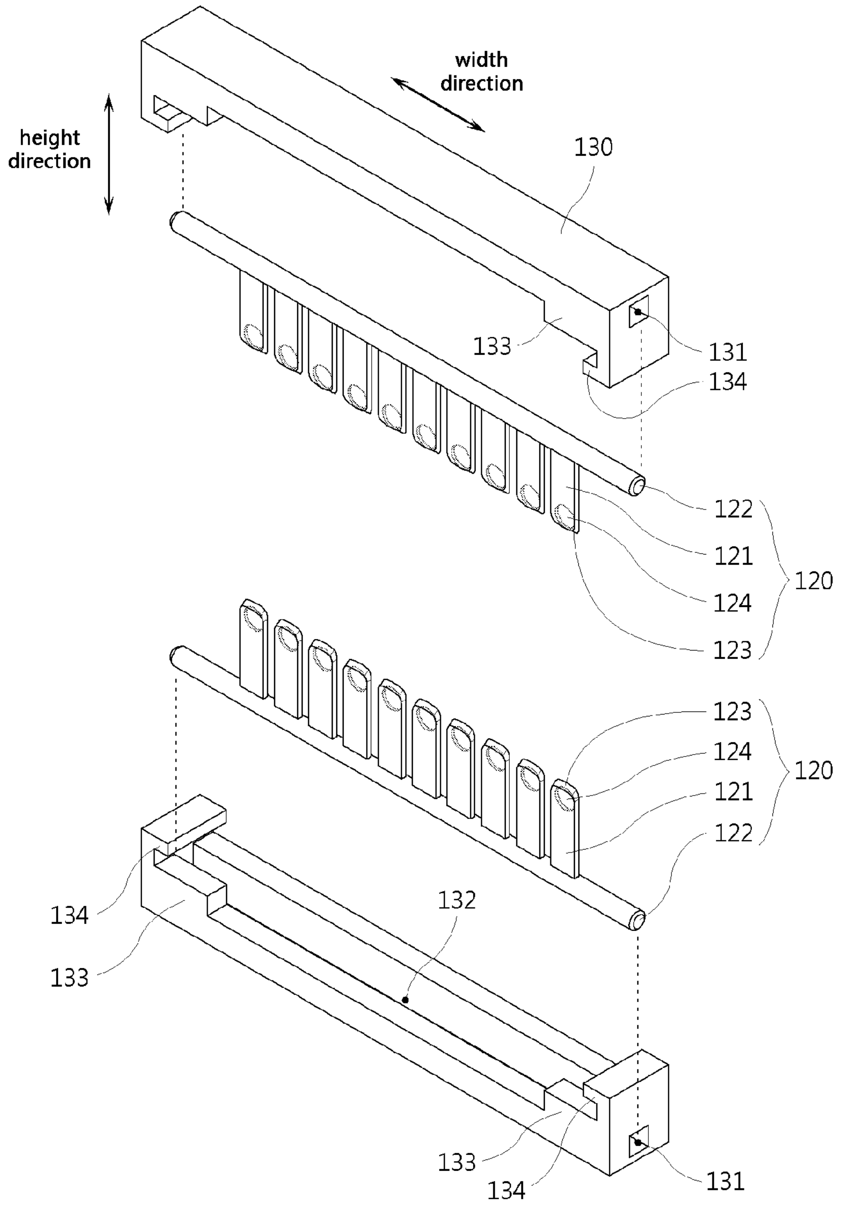
FIG. 2 is an exploded perspective view of a pin-assy and a provider according to the present invention.

Meanwhile, the provider 130 operates to sequentially provide the pin-rows to the well-rows arranged in the length direction. In realizing the provider 130, for example, the structure and the like in which the motor is directly attached to the bar 122 and rotated may be adopted to move the pin-row. However, in the same manner as in the pin-assy 120 design, it is preferable to realize the above-described operation while having the simplest structure as much as possible in order to prevent the device from being unnecessarily excessively complicated. FIG. 2 shows an exploded perspective view of the pin-assy 120 and the provider 130 designed in this manner. In the embodiment of FIG. 2, the bar 122 of the pin-assy 120 may be rotatably coupled to the provider 130, and one end of the pin 121 may be immersed in or taken out from the well 111 by the rotation of the bar 122.

As described above, it is preferred that the membrane 112 is covered on the top surface of the body 110 to prevent the reagents immersed in the wells 111 from being separated. In the case where the membrane 112 exists, when the bar 122 is rotated by the movement of the provider 130 in the length direction, one end of the pins 121 is immersed in the wells 111 while crushing the membrane 112. In this case, however, when one end of the pins 121 is bluntly formed, there is a possibility that one end of the pins 121 is supported by the membrane 112 to disturb the rotation of the bar 122. In order to avoid this problem, as shown in FIG. 2, the pin 121 preferably includes a tearer 123 whose one end surface is inclined so that a tip thereof is sharply formed.

In this case, when the sample-stations 124 are formed together on a surface on which the tearer 123 is formed, the positions of the sample-stations 124 are raised too much, and therefore there is a possibility that the sample-stations 124 may not be sufficiently immersed in the reagent. To avoid this problem, it is preferable that the sample-station 124 is formed on the opposite side where the tearer 123 is formed.

Figure 3:
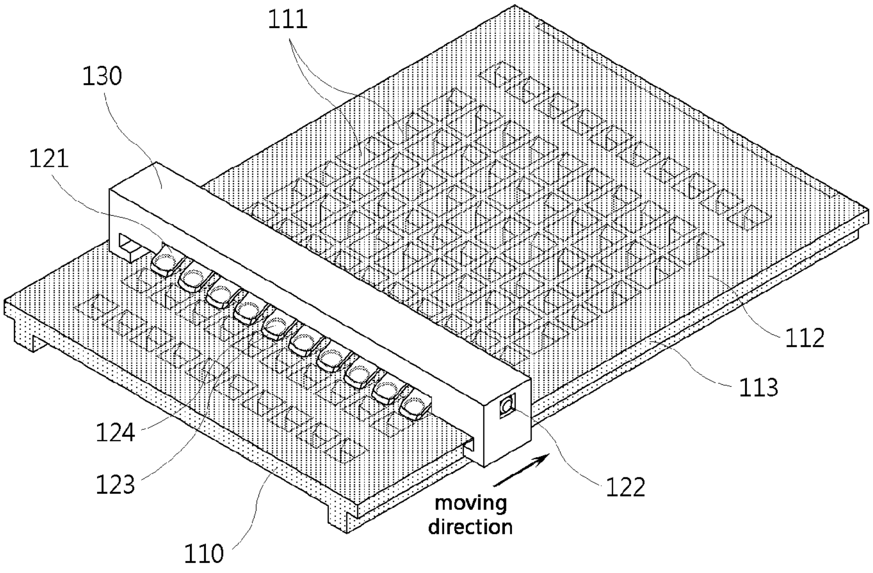
FIGS. 3 and 4 are assembled perspective views of the cartridge for sandwich ELISA according to the present invention.
Figure 3:
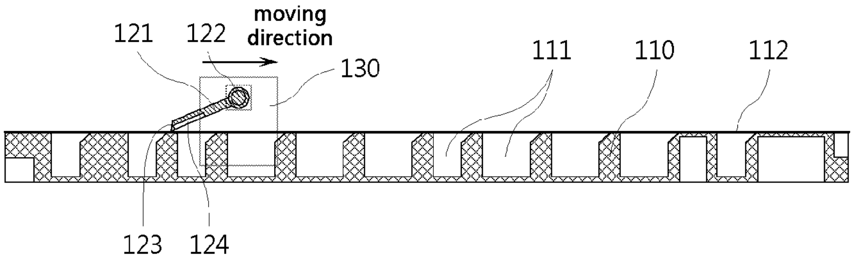
Figure 4:
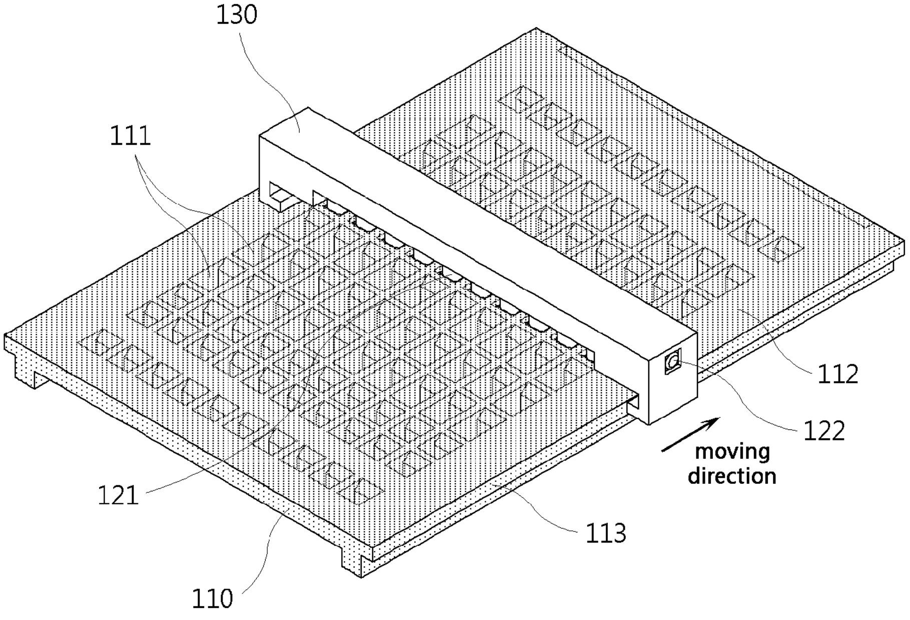
Figure 4:
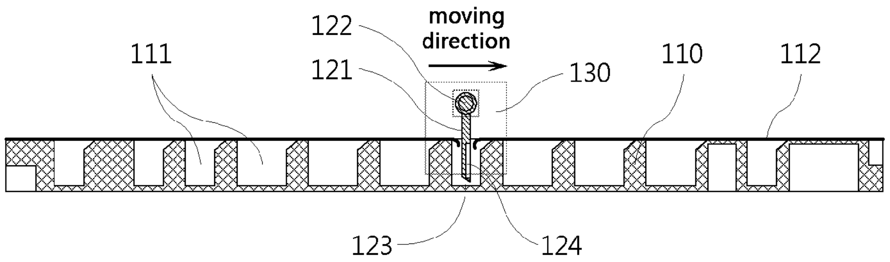
Figure 5:
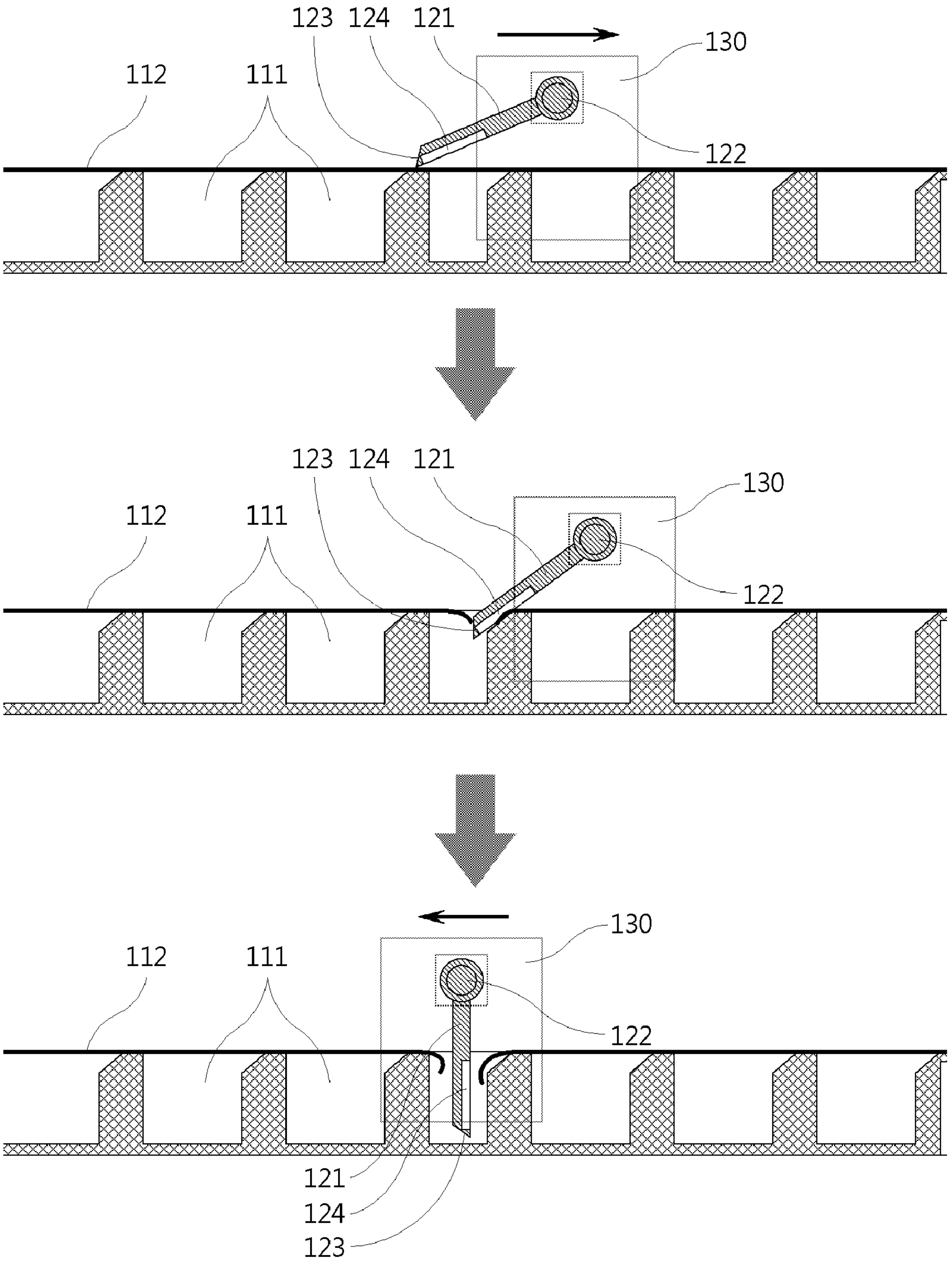
FIG. 5 is a cross-sectional view of the cartridge for sandwich ELISA according to the present invention.

FIGS. 3 and 4 are assembled perspective views of the cartridge for sandwich ELISA according to the present invention, and FIG. 5 is a cross-sectional view of the cartridge for sandwich ELISA according to the present invention, and shows in detail a process of rotating the bar 122 by the movement of the provider 130 in the length direction. As shown in the top view of FIGS. 3 and 5, when the provider 130 is arranged at a position where the wells 111 do not exist on the body 110, the pins 121 protrude in an opposite direction to the traveling direction of the provider 130 to be supported on the top surface of the body 110. When the provider 130 moves in the length direction, and as shown in the intermediate view of FIGS. 4 and 5, the provider 130 is arranged at the position where the wells 111 exist on the top surface of the body 110, the pins 121 are no longer supported on the top surface of the body 110, and thus the bar 122 is naturally rotated by the self-weight of the pins 121, such that one end of the pins 121 is immersed in the wells 111.

In view of the above operation process, it may be seen that the provider 130 may be formed to be movable only in one direction with respect to the length direction of the body 110. However, the provider 130 is preferably formed to be movable in both directions with respect to the length direction of the body 110, which will be described in detail as follows. When the provider 130 moves in the same direction as the arrow in the top view of FIG. 5 and reaches the same position as the intermediate view of FIG. 5, the pin 121 is dropped by its self-weight to be immersed in the well 111. However, as shown in the intermediate view of FIG. 5, one end of the pin 121 is immersed in the well 111, but the immersed depth may be shallow. At this time, if the water level of the reagent immersed in the well 111 is insufficient, a problem may occur in which the reaction between the capture antibody and the reagent is not properly performed. At this time, in the same state as the intermediate view of FIG. 5, if the provider 130 moves only slightly in the same direction as the arrow of the bottom view of FIG. 5, that is, in an opposite direction to the previous direction, the pin 121 is hooked on a wall surface of the well 111 and thus is rotated slightly in an opposite direction to the dropped direction. In this process, one end of the pin 121 may be deeply immersed in the well 111. As such, the provider 130 travels in one traveling direction on the whole, but needs to travel in a slightly opposite direction so that the pin 121 is deeply immersed in the well 111 in the overall direction. Accordingly, the provider 130 is preferably formed to be movable in both directions with respect to the length direction of the body 110.

The structures of the pin-assy 120 and the provider 130 of the present invention designed in a simplified structure while being able to realize all of these operations will be described again in more detail with reference to FIG. 2.

As described above, the pin-assy 120 is formed in a form in which a plurality of the pins 121 are fixedly arranged in a single bar 122 in a row. At this time, as shown in FIG. 2, the provider 130 may be in a form in which a pair of holes 131 is formed on both ends of thereof in the width direction and grooves 132 communicate with the pair of holes 131 and extend in the width direction. Accordingly, as shown in the bottom view of FIG. 2, the bar 122 is accommodated in the groove 132 and both ends of the bar 122 are fitted into the pair of the holes 131 to couple the pin-assy 120 to the provider 130. By adopting such a coupling structure, the replacement of the pin-assy 120 with respect to the provider 130 can be made very easily.

In this way, the pin-assy (120) is free to move in the width direction in the process of allowing both ends of the bar 122 to fit into the holes 131 at both ends of the provider 130, and therefore is likely to be arranged at a position deviating from a fixed position. At this time, since the plurality of pins 121 are fixedly arranged in line with the rows of the wells 111, when the pin-assy 120 itself deviates from the fixed position, the pins 121 are not correctly immersed in the wells 111. In order to prevent such a problem, the provider 130 may have a pair of guides 133, that regulates the rotation of the pins 121, provided on the opposite side of the traveling direction of both ends in the width direction. A width between the pair of the guides 133 is formed to be the same as that of a row of any one of the wells 111. Therefore, when the pins 121 deviate from the fixed positions corresponding to the positions of the wells 111 in the width direction, the rotational movement of the pins 121 is regulated by the guide 133. Therefore, as a result, it is possible to prevent the pins 121 from deviating from the fixed positions corresponding to the positions of the wells 111 in the width direction by the guide 133.

Meanwhile, as the structure in which the provider 130 is movably coupled in the length direction with respect to the body 110, the provider 130 may employ a rail structure as shown in FIG. 1 or the like. Describing in more detail, a pair of rails 113 extending in a length direction is formed at both ends of the body 110 in the width direction, and a slider 134 is formed at a lower end of both ends of the provider 130 in the width direction to engage with the rail 113. Accordingly, when the rail 113 and the slider 134 engage with each other, the provider 130 may be formed to be slidably movable in the length direction on the body 110.

The present invention is not limited to the abovementioned exemplary embodiments, but may be variously applied. In addition, the present invention may be variously modified by those skilled in the art to which the present invention pertains without departing from the gist of the present invention claimed in the claims.

INDUSTRIAL APPLICABILITY

The present invention uses a cartridge for sandwich ELISA to prevent human errors by sequential and stepwise contact and reaction of antibodies and reagents with high accuracy. Accordingly, according to the present invention, since the accuracy, promptness, and efficiency of the sandwich ELISA are maximized, the utilization in medical and bio fields is very high.

The invention claimed is:

1. A cartridge (100) for sandwich ELISA, comprising:

a body (110) comprising a plurality of wells (111) arranged in rows and columns in a width direction and a length direction, respectively, the wells (111) having reagents accommodated therein, and formed on a top surface thereof;

a pin-assembly (120) that includes a plurality of pins (121) extending in one direction and having a capture antibody coated on some areas of one end thereof and a single bar (122) extending in the width direction and coupled to the other end of the pins (121) so that the pins (121) are arranged to correspond to positions of the plurality of wells (111) included in the row of wells; and a provider (130) that extends in the width direction to support the pin-assembly (120) and is movably formed in the length direction from the top surface of the body (110) to provide the row comprised of the pins (121) with the row comprised of the wells (111);

wherein the bar (122) is rotatably coupled to the provider (130), and the one end of the pin (121) is configured to be immersed in or taken out from the plurality of wells (111) by the rotation of the bar (122); the bar (122) being further configured to be rotated by the movement of the provider (130) in the length direction, wherein the pins (121) protrude in an opposite direction to a traveling direction of the provider (130) to be supported on the top surface of the body (110), when the provider (130) is arranged at a position where the wells (111) do not exist on the top surface of the body (110), wherein the one end of the pins (121) is immersed in the wells (111) by the rotation of the bar (122), when the provider (130) is arranged at a position where the wells (111) exist on the top surface of the body (110), and wherein the provider (130) is provided with a pair of holes (131) that is formed on both ends thereof in the width direction and grooves (132) that communicate with the pair of holes (131) and extend in the width direction so that the bar (122) is accommodated in the groove (132) and both ends of the bar (122) are configured to be fitted into the pair of holes (131) to replaceably couple the pin-assembly (120) to the provider (130).

2. The cartridge (100) for sandwich ELISA of claim 1, wherein the top surface of the body (110) is covered with a membrane (112) to prevent the reagents accommodated in the wells (111) from being separated, and the one end of the pins (121) is immersed in the wells (111) while crushing the membrane (112), when the bar (122) is rotated by the movement of the provider (130) in the length direction.

3. The cartridge (100) for sandwich ELISA of claim 2, wherein at least some of the plurality of pins (121) includes a tearer (123) whose one end surface is inclined so that a tip thereof is sharply formed.

4. The cartridge (100) for sandwich ELISA of claim 3, wherein the at least some of the plurality of pins (121) includes sample-stations (124) recessed in a dish form that are formed in some areas on which the capture antibody is coated.

5. The cartridge (100) for sandwich ELISA of claim 4, wherein the sample-station (124) are formed on an opposite side where the tearer (123) is formed.

6. The cartridge (100) for sandwich ELISA of claim 1, wherein the provider (130) is provided with a pair of guides (133) that is formed on a surface of an opposite direction to the traveling direction of the both ends thereof in the width direction, the pair of guides (133) regulating the rotation of the pins (121), and a width between the pair of guides (133) is formed to be the same as that of a row of any one of the wells (111) so that the guide (133) prevents the pins (121) from being deviated from a fixed position corresponding to the positions of the wells (111) in the width direction.

7. The cartridge (100) for sandwich ELISA of claim 1, wherein a pair of rails (113) extending in the length direction is formed at the both ends of the body (110) in the width direction, and sliders (134) are formed at lower ends of the both ends of the provider (130) in the width direction to engage with the rails (113) so that the rails (113) and the sliders (134) engage with each other to slidably move the provider (130) in the length direction on the body (110).

8. A sandwich ELISA device comprising the cartridge (100) of claim 1.

* * * * *